United States Patent
Clerc et al.

[11] Patent Number: 5,939,096
[45] Date of Patent: Aug. 17, 1999

[54] LIPOSOME DRUG-LOADING METHOD AND COMPOSITION

[75] Inventors: Stéphane Clerc, Castres, France; Yechezkel Barenholz, Jerusalem, Israel

[73] Assignee: Yissum Research Development Company of the Hebrew University of Jerusalem, Israel

[21] Appl. No.: 08/865,005

[22] Filed: May 29, 1997

Related U.S. Application Data

[63] Continuation of application No. 08/423,136, Apr. 18, 1995, abandoned.

[51] Int. Cl.[6] .................................................. A61K 9/127
[52] U.S. Cl. ............................................................. 424/450
[58] Field of Search ................... 424/450, 1.21, 424/9.321, 9.51, 417; 436/829; 264/4.1, 4.3

[56] References Cited

U.S. PATENT DOCUMENTS

| | | |
|---|---|---|
| 4,885,172 | 12/1989 | Bally et al. . |
| 5,047,245 | 9/1991 | Bally et al. . |
| 5,077,056 | 12/1991 | Bally et al. . |
| 5,192,549 | 3/1993 | Barenholz et al. .................. 424/450 |
| 5,316,771 | 5/1994 | Barenholz .......................... 424/450 |
| 5,376,452 | 12/1994 | Hope et al. ........................ 428/402.2 |
| 5,380,531 | 1/1995 | Chakrabarti ........................ 424/450 |

FOREIGN PATENT DOCUMENTS

| | | |
|---|---|---|
| 0361894 | 4/1990 | European Pat. Off. . |
| 191 824 B1 | 10/1993 | European Pat. Off. . |
| 92/02244 | 2/1992 | WIPO . |
| 93/00888 | 1/1993 | WIPO . |
| 95/35094 | 12/1995 | WIPO . |

OTHER PUBLICATIONS

Hope, BBA, p 55–65, 1985.
Chakrabarti, Biophys J. Biophysical Society, 61, p 223–234, 1992.
Mayer, BBA, 857, p. 123–126, 1986.
Clerc, S, and Barenholz, Y., "Loading of Amphipathic Weak Acids into Liposomes in Response to Transmembrane Calcium Acetate Gradients," *Biochem. et Biophys. Acta* 1240:257–265 (1995).
deGier, J., "Osmotic Behaviour and Permeability Properties of Liposomes," in *Chemistry and Physics of Lipids* (Paltauf, F., and Schmid, H.H.O., Eds.) Elsevier Scientific Publishers Ireland, Ltd., vol. 64, pp. 187–196 (1993).
Walter, A., et al., "Monocarboxylic Acid Permeation Through Lipid Bilayer Membranes", *J. Membrane Biol.* 77:255–264 (1984).
Bally, M., et al., "Uptake of safranine and other Lipophilic cations into model membrane systems in response to a membrane potential," *Biochim.Biophys.Acta* 812: 66–76 (1985).
Cramer, J., et al., "NMR Studies of pH–Induced Transport of Carboxylic Acids Across Phospholipid Vesicle Membranes," *Biochemical and Biophysical Research Communication* 75 (2): 295–301 (1977).
Deamer, D.W., and J.W. Nichols, "Proton–hydroxide permeability of liposomes," *Proc. Natl. Acad. Sci. USA* 80(1): 165–168 (1983).

(List continued on next page.)

*Primary Examiner*—Gollamudi S. Kishore
*Attorney, Agent, or Firm*—Susan T. Evans; Judy M. Mohr; Peter J. Dehlinger

[57] ABSTRACT

A method of stably encapsulating a weak acid drug in liposomes, at a high concentration, is disclosed. The method employs a proton shuttle mechanism involving the salt of a weak acid to generate a higher inside/lower outside pH gradient. The weak acid compound accumulates in liposomes in response to this gradient, and may be retained in the liposomes by cation-promoted precipitation or low permeability across the liposome transmembrane barrier. Also disclosed is a reagent combination for practicing the method, and a liposome composition formed by the method.

12 Claims, 7 Drawing Sheets

OTHER PUBLICATIONS

Deamer, D., et al. "The Response of Fluorescent Amines to ph–Gradients Across Liposome Membranes," *Biochem et Biophysica Acta* 274: 323–335 (1972).

Firth, G., et al., "Studies on the Use of Antimitotic Drugs Entrapped Within Liposomes and of Their Action on a Human Glioma Cell Line," *Journal Of The Neurological Science* 63: 153–165 (1984).

Harrigan, P., et al., "Accumulation Of doxorubicin and other lipophilic amines into large unilamellar vesicles in response to transmembrane pH gradients," *Biochim.Biophys.Acta* 1149: 329–338 (1993).

Hope, M., et al., "Production of large unilamellar vesicles by a rapid extrusion procedure. Characterization of size distribution, trapped volume and ability to maintain a membrane potential," *Biochim. Biophys. Acta* 812: 55–65 (1985).

Lasic, D., et al., "Transmembrane gradient driven phase transitions within vesicles: lessons for drug delivery," *Biochim. Biophys. Acta* 1239: 145–156 (1995).

Mayer, L., et al., "Uptake of antineoplastic agents into large unilamellar vesicles in response to a membrane potential," *Biochim. Biophys. Acta* 816: 294–302 (1985).

Nichols, J., et al., "Catecholamine Update and Concentration By Liposomes Maintaining pH Gradients," *Biochim. Biophys. Acta* 455: 269–271 (1976).

Yatvin, M.B., et al., "Clinical propects for liposomes," *Med. Phys.* 9(2): 149–175 (1982).

LIPOSOME DRUG-LOADING METHOD AND COMPOSITION

This application is a file-wrapper-continuation application Ser. No. 08/423,136, filed Apr. 18, 1995, now abandoned.

FIELD OF THE INVENTION

The present invention relates to a method of loading a weak-acid drug compound into liposomes, and to a liposome composition formed thereby.

REFERENCES

Barenholz, Y., et al., in *LIPOSOME TECHNOLOGY*, 2nd Edition, Vol. I (Gregoriadis, G., Ed.), pp. 527–616, CRC Press, Boca Raton (1993).

Barreto, J., et al., *Am. J. Physiol. G* 262:30–34 (1992).

Bassnett, S., et al., *Am. J. Physiol. C,* 258:171–178 (1990).

Bolotin, E. M., et al., *J. Liposome Res.* 4:455–579 (1994).

Blume, G., et al., *Biochimica et Biophysica Acta* 1149:180–184 (1993).

Cramer, J., et al., *Biochemical and Biophysical Research Communications* 75(2):295–301 (1977).

Grimes, P. A., et al., *Arch. Ophtalmol.* 100:635–639 (1982).

Haran, G., et al., *Biochim. Biophys. Acta* 1151:201–215 (1993).

Hunt, C. A., et al., *International Journal of Pharmaceutics* 8:101–110 (1981).

Jackson, C.-J. C., et al., *Anal. Biochem.* 165:114–127 (1987).

Kano, K., and Fendler, *Biochim. Biophys. Acta* 509:289–299 (1978).

Klopman, G., et al., *Antimicrobial Agents and Chemother.* 9:1807–1815 (1993).

Lasic, D. D., et al., *FEBS Lett.* 312:255–258 (1992).

Maiti, P., et al., *Int. J. Cancer* 3:17–22 (1988).

MacDonald, R. C., et al., *Biochim. Biophys-Acta* 1061:297–303 (1991).

Machy, P. et al., *Proc. Natl Acad. Sci. USA* 79:4148–4152 (1982a).

Machy, P. et al., *J. Immunol.* 129:2098–2102 (1982b).

Madden, T. D., et al., *Chem. Phys. Lipids* 53:37–46 (1990).

Martin, F. J., et al., PCT Patent Application U.S. Ser. No. 90/06034 for "Liposome Microreservoir Composition and Method" filed Oct. 19, 1990.

Neufeld, E. F., et al., In: *THE BIOCHEMISTRY OF GLYCOPROTEIN AND PROTEOGLYCANS*, (W. J. Lennarz, Ed.) Plenum Press, New York, pp. 241–261 (1980).

Nichols, J. W., et al., *Biochim. Biophys. Acta* 455:269–271 (1976).

Takács-Novák, K., et al., *J. Pharm. Sci.* 79:1023–1028 (1990).

Tsuji, A., et al., *Antimicrob. Agents Chemoth.* 32:190–194 (1988).

Vallée, F., et al., *Ther. Drug Monit.* 8:340–345 (1986).

Walter, A., and Gutknecht, *J. Membrane Biol.* 77:255–264 (1984).

Weinstein, J. N., et al., in *LIPOSOME TECHNOLOGY*, Vol. III (Gregoriadis, G., Ed.), pp. 183–204, CRC Press, Boca Raton (1984).

Willenberg, D. O., et al., *Aust. J. Exp. Biol. Med. Sci.* 59:135–141 (1982).

Wolosin, J. M., and Ginsberg, *Biochim. Biophys. Acta* 389:20–33 (1975).

BACKGROUND OF THE INVENTION

Liposomes have been proposed as carriers for a variety of therapeutic agents. Drug delivery systems utilizing liposomes offer the potential of improved delivery properties, including enhanced blood circulation time, reduced cytotoxicity, sustained drug release, and targeting to selected tissues.

In utilizing liposomes for drug delivery, it is generally desirable to load the liposomes to high encapsulated drug concentration. Rate of leakage of the drug from the liposomes should also be low, to preserve the advantages of drug delivery in liposome-entrapped form.

A variety of drug-loading methods are available for preparing liposomes with entrapped drug. In the case of many lipophilic drugs, efficient drug entrapment can be achieved by preparing a mixture of vesicle-forming lipids and the drug, e.g., in a dried film, and hydrating the mixture to form liposomes with drug entrapped predominantly in the lipid bilayer phase of the vesicles. Assuming the partition coefficient of the drug favors the lipid phase, high loading efficiency and stable drug retention can be achieved.

The same type of passive loading may also be employed for preparing liposomes with encapsulated hydrophilic compounds. In this case, the drug is usually dissolved in the aqueous medium used to hydrate a lipid film of vesicle-forming lipids. Depending on the hydration conditions, and the nature of the drug, encapsulation efficiencies of between about 5–20% are typically obtained, with the remainder of the drug being in the bulk aqueous phase. An additional processing step for removing non-encapsulated drug is usually required.

A more efficient method for encapsulated hydrophilic drugs, involving reverse evaporation from an organic solvent, has also been reported (Szoka, et al., 1980). In this approach, a mixture of hydrophilic drug and vesicle-forming lipids are emulsified in a water-in-oil emulsion, followed by solvent removal to form an unstable lipid-monolayer gel. When the gel is agitated, typically in the presence of added aqueous phase, the gel collapses to form oligolamellar liposomes with high (up to 50%) encapsulation of the drug.

In the case of ionizable hydrophilic or amphipathic drugs, even greater drug-loading efficiency can be achieved by loading the drug into liposomes against a transmembrane pH gradient (Nichols, et al., 1976; Cramer, et al., 1977). Typically the drug contains an ionizable amine group, and is loaded by adding it to a suspension of liposomes prepared to have a lower inside/higher outside pH gradient. Although high drug loading can be achieved by this approach (e.g., U.S. Pat. No. 5,077,056), the drug tends to leak out over time as the liposome transmembrane proton gradient decays.

The latter problem has been addressed, for drugs having an ionizable amine group, by loading the drug across an ammonium ion gradient (Haran, et al., 1993). Ammonium ions within the liposomes are in equilibrium with ammonia, which is freely permeable through the liposome membrane, and protons, which therefore accumulate as ammonia is lost from the liposomes, leading to a lower inside/higher outside pH gradient. After establishing the gradient, excess ammonium ions within the liposomes provide a reservoir of protons, to maintain the liposome pH gradient over time. This approach, however, is limited to drugs which are positively charged in their ionized state.

It would be desirable, therefore, to provide a liposome composition and method for stably loading, to high drug concentration, an ionizable drug which is negatively charged in its ionized state.

SUMMARY OF THE INVENTION

The present invention includes, in one aspect, a method of forming liposomes having a higher inside/lower outside pH gradient. The gradient is established by preparing a suspension of liposomes in an aqueous solution containing a salt of a weak acid which is capable of freely permeating the liposome membrane. The suspension is then treated to produce a higher inside/lower outside concentration gradient of the weak acid. The weak acid is allowed to distribute between inner and outer compartments, acting as an inside-to-outside proton shuttle to generate a higher inside/lower outside pH gradient.

Exemplary weak acids for use in the invention include carboxylic acids such as formic acid, acetic acid, propanoic acid, butanoic acid, pentanoic acid, and substituted derivatives thereof.

In a related aspect, the invention provides a method for loading a weak-acid compound into liposomes having a higher inside/lower outside pH gradient. Loading is carried out by adding the weak acid compound to a suspension of liposomes having a higher inside/lower outside gradient of a salt of a weak acid which includes the given cation. The protonated form of the weak acid salt acts as an inside-to-outside proton shuttle to generate a higher inside/lower outside pH gradient to drive loading of the weak acid compound into the liposome interior.

Weak acid compounds for loading by the present method include ibuprofen, tolmetin, indomethacin, phenylbutazone, meclofenamic acid, piroxicam, ciprofloxacin, and nalidixic acid.

In one general embodiment, the weak acid compound has a low water solubility in the presence of a given cation, typically a multivalent cation, allowing compound loading to high concentrations in precipitated form within the liposomes.

In another general embodiment, the protonated form of the weak acid compound is readily able to permeate the liposome transmembrane barrier only at a temperature above the phase transition temperature of the liposomes. The compound is loaded at a temperature above this phase transition temperature, and the suspension is stored at a temperature below the phase-transition temperature.

In still another aspect, the invention includes a reagent combination for use in producing a suspension of liposomes with an encapsulated weak-acid compound. The combination includes liposomes of the type described above, having a higher inside/lower outside gradient of a weak acid, the weak acid compound to be loaded, and means for retaining compound in the liposomes after compound loading.

Also included in the invention is a liposome composition produced by compound loading with the above combination, for use in delivering the compound, e.g., by intravenous administration.

These and other objects and features of the invention will become more fully apparent when the following detailed description is read in conjunction with the accompanying figures and examples.

DETAILED DESCRIPTION OF THE INVENTION

I. Definitions

Figure 1:
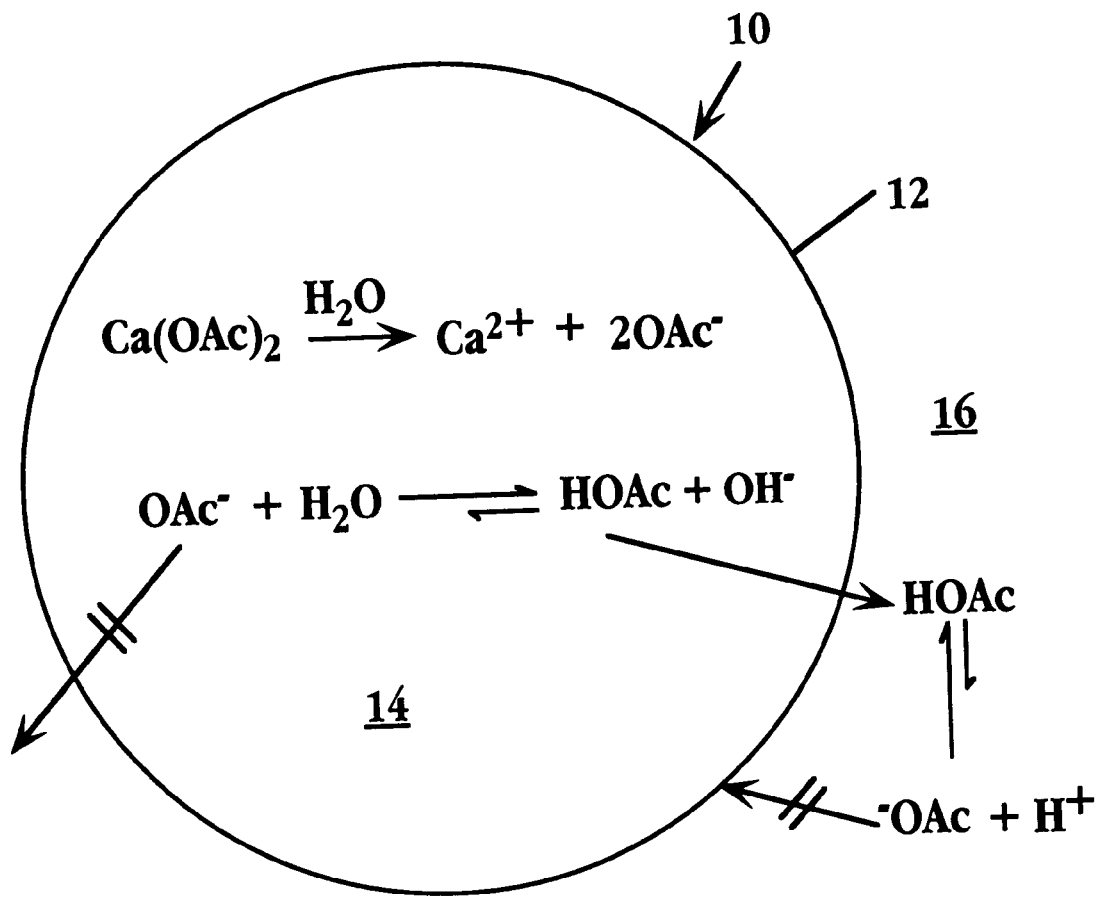
FIG. 1 a schematic illustration of solute-transport events responsible for forming a higher inside/lower outside pH gradient, in accordance with the invention.

The following terms, as used herein, have the meanings as indicated:

A "weak acid" is a compound having an acid dissociation constant less than about $10^{-4}$. Typically, and as used herein, weak acids are compounds which, when dissolved in water, form mildly acidic solutions, that is, solutions with pH values between about 3–6. The weak acid should also possess a permeability coefficient larger than $10^{-4}$ cm/s for liposome bilayers, to ensure rapid transmembrane movements.

Typically, weak acids for use in the present invention are organic acids containing at least one carboxyl group. Exemplary weak acids include formic acid, acetic acid, propanoic acid, butanoic acid, pentanoic acid, and substituted forms thereof.

The term "weak acid" is distinct from "weak acid compound", which refers to a compound intended for loading into the liposomes, as described below.

"Substituted forms thereof" or "substituted weak acid" refers to a weak acid compound as defined above, generally having a straight or branched chain skeleton and containing one or more R groups substituted for a hydrocarbon (C—H) bond. A preferred substituent is lower alkyl, although any functional group which does not (i) adversely affect the $pK_a$ of the weak acid or (ii) markedly decreases the compound's solubility in water is suitable.

"Weak acid salt" refers to the conjugate base of the weak acid. As used herein, weak acid salt refers to both the conjugate base of the weak acid and to any accompanying counterions. Preferably, a weak acid salt for use in the present invention is water soluble at high concentrations. The counterion or cation should be practically lipid-membrane impermeable (having a permeability coefficient, P, of less than about $10^{-12}$ to $10^{-11}$ cm/s). The counterion may be monovalent or multivalent.

A "weak acid compound" as used herein refers to a compound intended for loading into liposomes, and which also contains at least one carboxy group. The $pK_a$ of the weak acid compound is typically less than about 5. The weak acid compound may also contain one or more functional groups in addition to the carboxy function, although the presence of such functional group should not significantly alter the acidity of the compound from that of its non-functionalized counterpart. Weak acid compound refers to both the compound in its protonated form and to any salt forms thereof. A salt of a weak acid compound may be accompanied by any pharmaceutically acceptable counterion.

A "strong acid" typically refers to a compound having an acid dissociation constant of greater than 1.

A "liposome-entrapped" or "liposome-encapsulated" compound refers to a compound which is sequestered, at least in part, in the internal compartment of liposomes or within the liposomal membrane.

A "higher inside/lower outside pH gradient" refers to a transmembrane pH gradient between the interior of liposomes (higher pH) and the external medium (lower pH) in which the liposomes are suspended. Typically, the interior liposome pH is at least 1 pH unit greater than the external medium pH, and preferably 2–4 units greater.

II. Preparation of pH Gradient Liposomes

This section describes the preparation of a suspension of liposomes having a higher inside/lower outside pH gradient, in accordance with the invention.

A. Lipid Components

The liposomes of the invention are composed of vesicle-forming lipids, generally including amphipathic lipids having both hydrophobic tail groups and polar head groups. A characteristic of a vesicle-forming lipid is its ability to either (a) form spontaneously into bilayer vesicles in water, as exemplified by the phospholipids, or (b) be stably incorporated into lipid bilayers, by having the hydrophobic portion in contact with the interior, hydrophobic region of the bilayer membrane, and the polar head group oriented toward the exterior, polar surface of the membrane. A vesicle-forming lipid for use in the present invention is any conventional lipid possessing one of the characteristics described above.

The vesicle-forming lipids of this type are preferably those having two hydrocarbon tails or chains, typically acyl groups, and a polar head group. Included in this class are the phospholipids, such as phosphatidylcholine (PC) or lecithin, phosphatidylethanolamine (PE), phosphatidyl-N-methylethanolamine (PE-Me), phosphatidyl-N,N-dimethylethanolamine (PE-diMe), phosphatidyl serine (PS), phosphatidic acid (PA), phosphatidylglycerol (PG), a polyol-containing phosphatide, and phosphatidylinositol (PI), where the two hydrocarbon chains are typically between about 14–22 carbon atoms in length, and have varying degrees of unsaturation. Preferred phospholipids include PE and PC.

The above-described lipids and phospholipids whose acyl chains have a variety of degrees of saturation can be obtained commercially, or prepared according to published methods.

Lipids for use in the present invention may be relatively "fluid" lipids, meaning that the lipid phase has a relatively low gel-to-liquid-crystalline phase transition temperature, e.g., at or below room temperature, or alternately, relatively "rigid" lipids, indicating that the lipid has a relatively high gel-to-liquid-crystalline phase transition temperature, e.g., at temperatures up to about 50° C. As a general rule, the more rigid, i.e., saturated lipids, contribute to greater membrane rigidity in the lipid bilayer structure, and thus to more stable drug retention after active drug loading. Preferred lipids of this type are those having phase transition temperatures above about 37° C.

The liposomes may additionally include lipids that can stabilize a vesicle or liposome composed predominantly of phospholipids, such as cholesterol in a mole ratio of 25 to 45 mole percent.

Liposomes used in the invention preferably contain between 30–75 percent phospholipids, preferably phosphatidylcholine (PC), 25–40 percent cholesterol, and 0–20 percent polymer-derivatized lipid, expressed on a molar percent basis. One exemplary liposome formulation, for example, contains 60 mole percent phosphatidylcholine and 40 mole percent cholesterol, as described in Example 1.

The liposomes may optionally include a coating or a graft of a hydrophilic polymer chain, for extended circulation lifetime in the bloodstream (see U.S. Pat. No. 5,130,556). Such liposomes are typically prepared by including in the vesicle-forming lipid, 1–20 mole percent of a diacyl-chain lipid, e.g., a phospholipid, derivatized with the hydrophilic polymer, e.g., polyethylene glycol (PEG) having a molecular weight between 1–10 Kdaltons, preferably 2–5 Kdaltons. Methods for preparing PEG-derivatized phospholipids are detailed, for example, in the above cited U.S. Pat. No. 5,013,556.

Other hydrophilic polymers which may be suitable include polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethylcellulose. Phospholipid polymer conjugates of these polymers are described in WO 94/02271, published Sep. 3, 1994.

One exemplary "rigid" polymer-grafted liposome formulation is formed of polyethylene glycol conjugated phosphatidylethanolamine, PEG-PE, hydrogenated soy phosphatidylcholine (HSPC) and cholesterol in a weight ratio of 1:3:1. Two exemplary polymer coated fluid liposome compositions contain the components PEG-PE, egg phosphatidylcholine (EPC), and cholesterol, in corresponding molar ratios of 6:56:38 and 6:62:32.

The liposomes may optionally be prepared to contain additional surface groups, such as antibodies or antibody fragments (Machy, et al., 1982(a); Machy, et al., 1982(b)), small effector molecules for interacting with cell-surface receptors (Neufeld, et al., 1980), antigens (Willenberg, et al., 1982), and other like compounds for achieving desired target-binding properties to specific cell populations. Here the lipid component included in the liposomes would include either a lipid derivatized with the targeting molecule, or a lipid having a polar-head chemical group that can be derivatized with the targeting molecule in preformed liposomes, according to known methods.

B. Liposome Preparation

Liposomes for use in the invention may be prepared by a variety of techniques. In a typical procedure, a mixture of liposome-forming lipids is dissolved in a suitable organic solvent and evaporated in a vessel to form a thin film. The film is then covered with an aqueous medium containing the solute species that will form the aqueous phase in the liposome interior spaces, in the final liposome preparation. The lipid film hydrates to form multi-lamellar vesicles (MLVs) having heterogeneous sizes typically between about 0.1 to 10 microns.

In the general case, the liposomes are prepared in a solution containing a weak acid salt, such as sodium or calcium acetate, sodium or calcium formate, or other suitable salt of a weak organic acid, such as salts of propanoic, butanoic, or pentanoic acid, and derivatives thereof, as defined in Section I. The weak acid is one which, in its uncharged or undissociated form, is readily able to permeate the transmembrane barrier of the liposomes. The acid salt also preferably has a high solubility in water, e.g., greater than about 300 mg/ml. The hydration medium is preferably at least 50 mM weak acid salt, and typically between 50–300 mM. The medium is adjusted, e.g., by addition of acid, to a pH of between 5 and 7, but contains no additional buffering species.

As will be described below, the compound to be encapsulated may have a low aqueous solubility in the presence of certain cations, typically multivalent cations such as $Ca^{+2}$. In such case, the salt of the weak acid preferably includes the salt of that cation and the weak acid.

After liposome formation, the vesicles may be sized to achieve a size distribution of liposomes within a selected range, according to known methods. The liposomes are preferably uniformly sized to a selected size range between 0.04 to 0.25 $\mu$m. Small unilamellar vesicles (SUVs), which are single-walled vesicles typically in the 0.04 to 0.08 $\mu$m range, can be prepared by extensive sonication or homogenization (Martin, et al., 1990) of the liposomes.

Homogeneous sized liposomes having sizes in a selected range between about 0.08 to 0.4 microns, e.g., 0.07–0.12 microns, can be readily produced by extrusion through defined pore-size membranes, e.g., polycarbonate membranes, having defined pore size membranes with selected pore sizes ranging from 0.03 to 0.5 microns, typically, 0.05, 0.08, 0.1, or 0.2 microns. The pore size of the membrane corresponds roughly to the largest size of liposomes produced by extrusion through that membrane, particularly where the preparation is extruded two or more times through the same membrane, as described in Example 1.

The sizing is preferably carried out in the original lipid-hydrating buffer, so that the liposome interior spaces retain this medium throughout the initial liposome processing steps.

C. Formation of Liposome pH Gradient

After sizing, the external medium of the liposomes is treated to produce a higher inside/lower outside concentration gradient of the weak acid salt. This may be done in a variety of ways, e.g., by (i) diluting the external medium, (ii) dialysis against the desired final medium, (iii) molecular-sieve chromatography, e.g., using Sephadex G-50, against the desired medium, or (iv) high-speed centrifugation and resuspension of pelleted liposomes in the desired final medium.

The external medium preferably contains (i) a buffer, e.g., a 5–50 mM buffer having a pH the same as or similar to the pH of the original hydration medium, and (ii) solute species effective to raise the osmolality of the external medium to close to that of the internal medium, e.g., 200–300 osm/kg. The buffer is preferably one, like histidine, MES or TRIS, which is relatively impermeant, and which exerts maximum buffering capacity in the pH 5–7 range.

The solute species for external-medium osmolality is preferably either the salt of a strong acid, e.g., physiological saline, or a mono- or di-saccharide, such as sucrose, glucose, or mannitol. The latter type of solute is preferred where it is desired to store the liposomes by lyophilization, in which case the saccharide functions as a cryoprotectant to minimize liposome damage during freezing and rehydration.

After adjusting the external medium to produce a higher inside/lower outside concentration gradient of the weak acid salt, the weak acid is allowed to distribute between inner and outer liposome compartments, with the weak acid salt acting as an inside-to-outside proton shuttle, until an equilibrium higher inside/lower outside pH gradient is formed.

FIG. 1 illustrates the proton-shuttle mechanism by which the pH gradient is formed. The figure shows a liposome 10 having a bilayer membrane 12 and having encapsulated therein, the salt of a weak acid, in this case, the calcium salt of acetate, with the acetate anion being in equilibrium with the uncharged (protonated) form of the acid. The bilayer membrane serves as a partition between the liposome inner compartment, indicated at 14, and an outer bulk phase suspension medium 16.

As indicated, acetate is effectively impermeant to the liposome membrane in its charged form, but readily passes through the membrane in its protonated form. Because of the weak-acid gradient across the liposome membrane, protonated weak acid shows a net migration in an inside-to-outside direction, acting to shuttle protons out of the liposomes. This leads to an increased concentration of hydroxyl ions inside the liposomes and an increased proton concentration outside the liposomes.

The final pH gradient formed across the membrane will depend on the distribution of weak acid species in the inner and outer compartments of the suspension. In considering the distribution of a weak acid between the inside and the outside compartments, ions from the dissociation of a weak acid are unable to cross the lipid bilayer, while the undissociated neutral molecules are readily permeable ($P > 10^{-4}$ cm/s). The latter assumption implies that the permeation kinetics is fast ($t_{1/2} < 10$ ms), and that the system reaches equilibrium in less than one second.

At equilibrium the concentration of the undissociated form is uniform within the entire suspension (i.e., the same in both internal and external compartments). Thus, according to the acid-base equilibrium, the following relationships hold true:

$$[A^-]_{out}/[A^-]_{in} = [H^+]_{in}/[H^+]_{out} \text{ and,}$$

$$C_{out}/C_{in} = ([H^+]_{in}/[H^+]_{out}) \times ((K_a + [H^+]_{out})/(K_a + [H^+]_{in})).$$

In the above equations, the subscripts "in" and "out" refer to the internal and external compartments, respectively, $K_a$ is the dissociation constant of the weak acid, and for a given compartment, C is the total concentration of the acid, [$A^-$] is the concentration of the conjugate base of the weak acid, and [$H^+$] is the proton concentration.

These two expressions can be simplified when the pH's are much higher than the acid $pK_a$. Under these conditions, $K_a$ is much larger than the proton concentrations, and the undissociated acid concentration is negligible. This simplifies the above equation to $C_{out}/C_{in}=[H^+]_{in}/[H^+]_{out}$.

Based on the above equation, the internal pH can be expressed in terms of the external pH and concentration ratio of weak acid inside and outside the liposomes, as follows: $pH_{in}=pH_{out}+\log_{10}(C_{in}/C_{out})$.

Figure 2A:
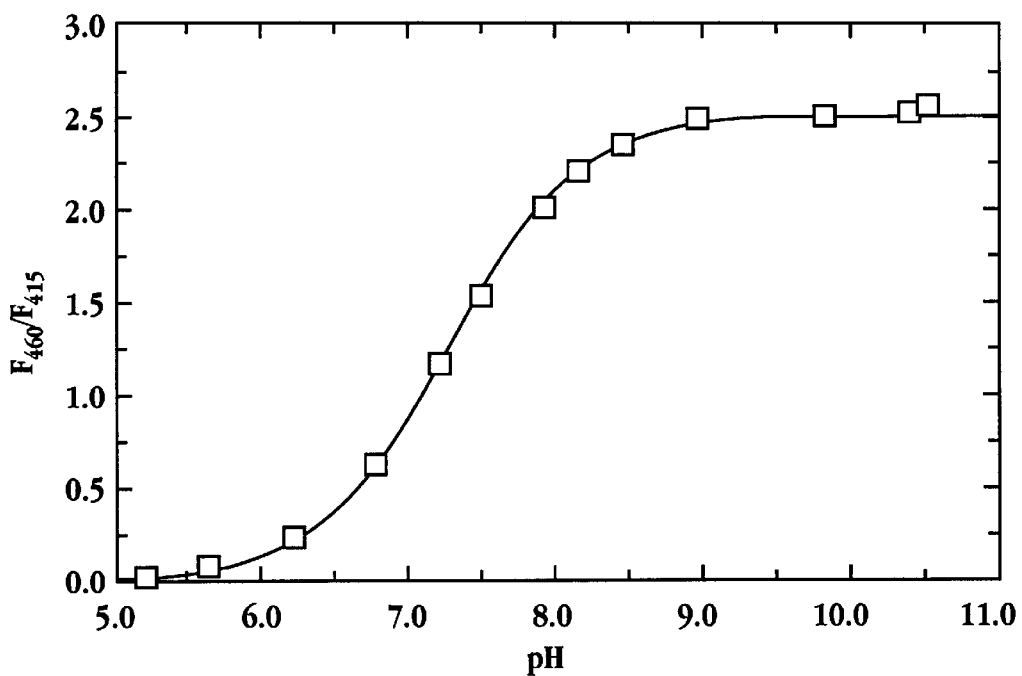
FIG. 2A is a plot showing the pH dependence of the 460 nm/415 nm excitation ratio for pyranine (1 $\mu$M, 507 nm emission) dissolved in 120 mM calcium acetate solutions over a pH range between 5.2 to 10.5.

The model was verified by the study detailed in Example 2. Briefly, a suspension of liposomes containing encapsulated pyranine and 150 mM sodium acetate was prepared and treated to (i) remove non-entrapped pyranine and (ii) exchange the external medium for one having a selected outer concentration of sodium acetate, with sodium sulfate being used to bring the external medium to iso-osmolarity. The internal pH of the liposomes was determined using a two-wavelength isosbestic-point method (Barreto, et al., 1992; Bolotin, et al., 1994), measuring the fluorescence emission intensity at 507 nanometers with excitation wavelengths of 460 and 415 nm. Excitation at 460 nm is pH-sensitive, while at 415 nm, emission is a function of the pyranine concentration only, so that the ratio of fluorescent emission at the two excitation wavelengths serves as an indicator of pH, as illustrated in FIG. 2A.

The acetate concentration in the external medium was adjusted by dilution of the liposomes in a suspension containing 120 mM sodium sulfate and the acetate salt used to prepare the liposomes; or alternatively, by gel-exclusion chromatography on Sephadex G-50 minicolumns preequilibrated with 120 mM sodium sulfate.

Figure 2B:
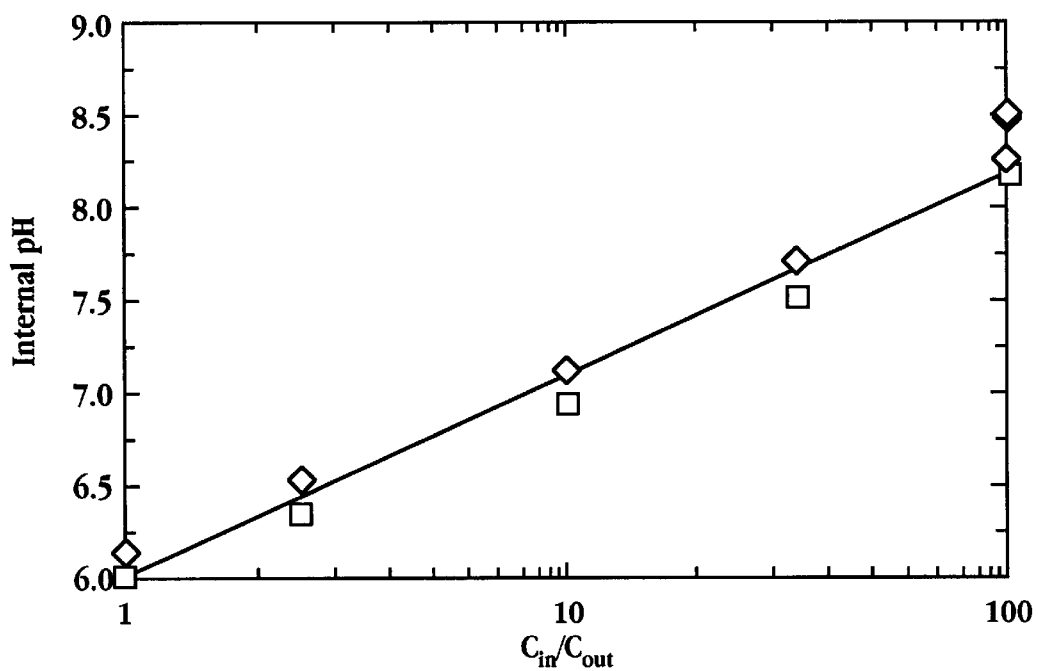
FIG. 2B is a plot showing changes in internal liposomal pH as a function of the ratio of internal to external acetate salt concentration as determined by pyranine fluorescence (diamonds: calcium acetate; squares: sodium acetate)

Internal pH values were calculated from the entrapped pyranine fluorescence as described in Example 1C. As seen in FIG. 2B, the internal pH was found to be linearly dependent on the logarithm of the acetate concentration ratios, where $pH=6.03+1.07\times\log (C_{in}/C_{out})$. The rise of the internal pH was very fast and determined to be less than 10s.

The pH increase was dependent only on the ratio of the internal-to-external concentrations of acetate, and showed no dependence on the nature of the counterion (e.g., sodium or calcium). The lack of pH dependence up on the nature of the counter ion is reasonable as the permeability coefficients of both sodium and calcium are very small.

It will be appreciated from the above that the pH gradient across the liposomes is self-regulating and self-sustaining, i.e., not degraded by leakage of protons into the liposomes or hydroxyl ions out of the liposomes after the gradient is formed. This feature can be appreciated from the proton shuttle mechanism illustrated in FIG. 1. Here it is assumed that a pH gradient has been established and the liposomes are stored over an extended period in suspension. During storage, as hydroxyl ions leak out from the liposomes into the external medium, and as protons leak into the liposomes from the external medium, the equilibrium between charged and protonated form of the weak acid (acetate) in the liposomes shifts toward the protonated form, increasing the level of proton shuttling out of the liposomes, acting to restore the pH gradient.

III. Method of Drug Loading

The pH gradient liposomes formed as above are used in loading a weak-acid compound into the liposomes, according to another aspect of the invention. In this method, the compound is added to a suspension of the pH gradient liposomes, and the suspension is treated under conditions effective to load weak acid compound within the liposomes.

A. Mechanism of Compound Loading

Figure 3:
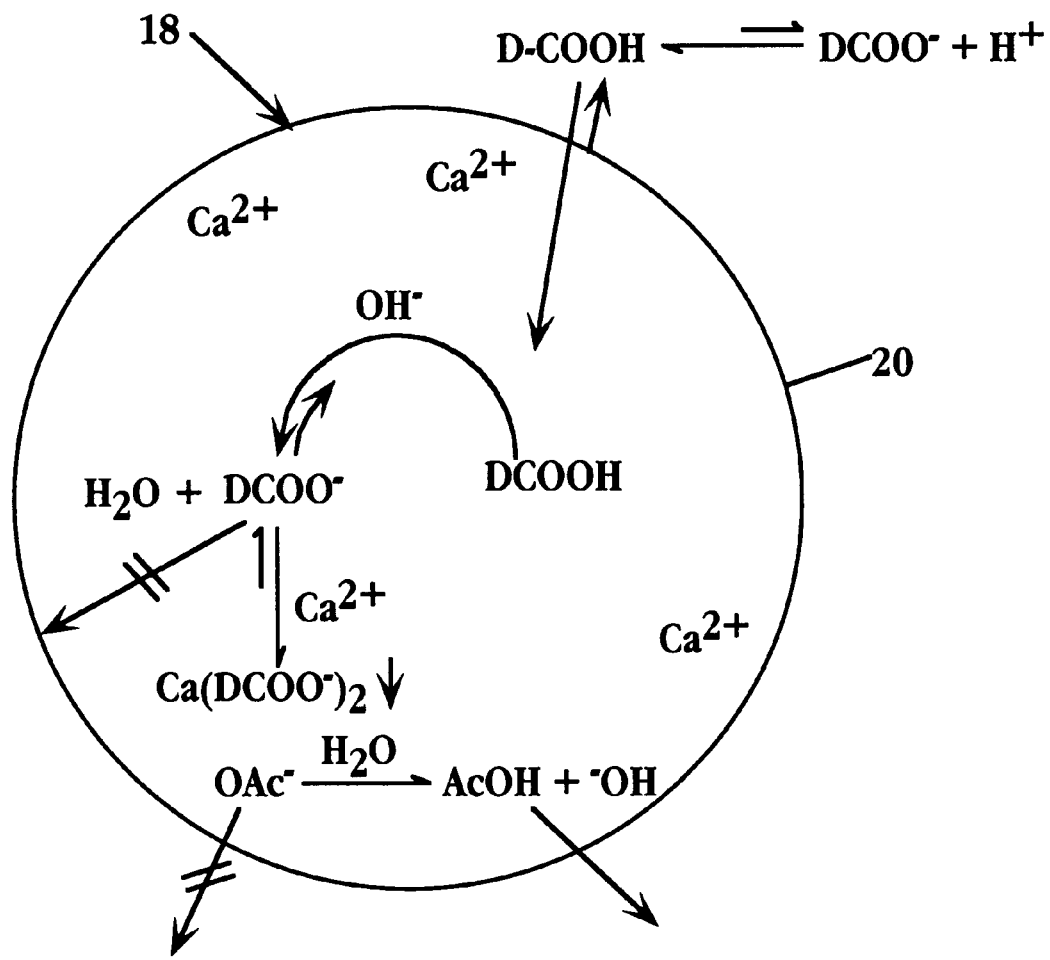
FIG. 3 is a schematic illustration of the loading of a weak acid drug, "D—COOH", into liposomes against a higher inside/lower outside pH gradient established by the method of the present invention.

FIG. 3 illustrates the mechanism of drug loading into liposomes, in accordance with the method. The figure shows a liposome 18 having a bilayer membrane 20 and a higher inside/lower outside pH gradient, by virtue of a higher inside/lower outside gradient of a weak acid, i.e., the anion of the weak acid, in this case the acetate anion.

The bottom of the figure shows the mechanism by which a higher inside/lower outside pH gradient is formed, as described in Section II. The upper part of the figure shows the mechanism of loading of the weak acid compound, indicated as "D—COOH". The compound, which is present originally only in the external compartment, is shown in equilibrium in this compartment between negatively charged and uncharged, protonated forms, with lower pH favoring the latter form. As indicated, the compound is able to pass through the liposome membrane only in its protonated form. In the absence of a pH gradient, the compound would equilibrate to equal concentrations on both sides of the membrane. Because of the higher internal pH, the equilibrium between the charged and uncharged form of the compound is shifted toward the charged, nonpermeable form, leading to net loading of the compound in the liposomes. Assuming the compound remains in solution in its liposome-loaded form, the extent of liposome loading for weak acid compounds is governed by the Henderson-Hasselbach relationship:

$$\log [H^+]_o/[H^+]_i = pH_i - pH_o = \Delta pH_{(i-o)} = \log (A_i/A_o) + \log (V_o/V_i),$$

which can be rearranged to give the following:

$$\log (A_i/A_o) = \Delta pH_{(i-o)} - \log (V_o/V_i),$$

where $V_o/V_i$ is the ratio of external volume to internal volume and $A_i/A_o$ is the ratio of total amount of weak acid compound inside and outside the liposomes.

By way of example, with a pH gradient of 4 pH units, and an outside-to-inside volume ratio of 100:1, a theoretical loading factor of 100:1 inside:outside is possible. Based on these considerations alone, it will be appreciated that it is possible to achieve substantially 100% loading efficiency, i.e., loading of substantially all of the compound present into the liposomes, by proper selection of the initial external concentration of compound in relation to the known inside/outside volume ratio of the liposomes, which can be estimated.

As noted above, the Henderson-Hasselbach relationship applies only in the case where the transported molecules are in solution. Preferably, the compound loaded is also one which has a low water solubility in the presence of a selected cation, such as a multivalent cation, as exemplified by $Ca^{+2}$ in the drawing, where this cation can be the cation of the salt of the weak acid used in forming the pH gradient.

The low solubility of the compound in the presence of the cation means that precipitation of the compound, and entrapment of the compound in precipitated form, occurs at a relatively low concentration of loaded compound. In other words, the extent of drug loading required by the pH gradient effect, under the Henderson-Hasselbach relationship, is relatively low, since additional loaded drug is sequestered by precipitation involving a non-pH effect.

The solubility of a particular salt of a given weak acid compound can be determined by standard methods, for purposes of selecting a counterion which will lead to insoluble complex formation and enhanced drug entrapment.

In some cases, the weak acid compound, in associated form, is readily able to permeate the liposome transmembrane only at a temperature above the phase transition temperature of the liposomes. In such cases, loading of the compound into the liposomes is carried out at a temperature above the liposome phase transition temperature, and entrapment of the compound is effected by cooling the liposome suspension containing encapsulated compound below the lipid phase transition temperature. Entrapment carried out as described above offers prolonged stability to the encapsulated compound, particularly against degradative processes which might otherwise impact the compound in non-encapsulated form.

B. Drug Loading Method

Liposomes having a higher inside/lower outside pH gradient in response to a transmembrane difference in acetate ion concentration are prepared as described above. Typically, weak acid compounds to be loaded are added to the bulk medium at concentrations ranging from 1 $\mu$M–100 mM, with the concentration selected depending upon both the absolute quantity of drug intended for encapsulation and the degree of loading efficiency desired, as discussed above.

After adding the weak acid compound to the liposomes, the liposomes are treated under conditions effective to trap the compound within the liposomes. Conditions suitable for compound loading are those which (i) allow diffusion of the weak acid compound, with such in an uncharged form, into the liposomes, (ii) lead to a desired final loading concentration and efficiency, and (iii) provide a self-sustaining pH gradient after drug loading.

Considering the first of these requirements, the loading period may range from 1 minute to several hours, and is typically between 15–120 minutes, depending on permeability of the weak acid drug into the liposomes, temperature, and the relative concentrations of liposome lipid and drug. Where the compound is one which readily permeates the liposome membrane only above the phase transition temperature of the liposome lipids, e.g., 50° C., the loading is carried out above this temperature. After loading, the liposomes are cooled below the phase transition temperature, e.g., to a storage temperature between 4–24° C., such cooling acting to retard efflux of the loaded compound from the liposomes, independent of a pH gradient mechanism.

The final drug loading concentration and loading efficiency may be approximated from the Henderson-Hasselbach relationship, as discussed above. In addition to the considerations already discussed, the concentration of weak acid remaining after drug loading must be sufficient to maintain a high inside/low outside concentration gradient of the weak acid, preferably a ratio of at least 10:1. Thus, for example, if the initial concentration of weak acid is 150 mM, and the final concentration of loaded weak-acid compound is 50 mM, the final concentration of weak acid in the liposomes would be 100 mM (ignoring the loss of weak acid used in establishing the pH gradient), since capture of each molecule of compound within the liposomes, by deprotonating the compound, requires the shuttling of one proton out of the liposomes, and thus the efflux of one molecule of the weak acid from the liposomes. Assuming a $V_o/V_i$ ratio of 50, concentration gradient of weak acid after drug loading in this example would be 100:50/50, or 100:1, sufficient to maintain a inside to outside drug loading ratio of 100:1.

In addition, the excess weak acid in the liposomes after drug loading provides a reservoir for sustaining the pH gradient across the liposomes over an extended storage time, as the equilibrium between protonated and unprotonated forms of the encapsulated weak acid is shifted in response to hydroxyl ion efflux or proton influx over time, as described in Section II. Accordingly, drug efflux from the liposomes on storage is effectively uncoupled from proton influx or hydroxyl-ion efflux, allowing for stable compound storage in suspension form over an extended period.

C. Gradient Loading of Two Exemplary Weak Acid Compounds

To illustrate one embodiment of the present invention, two exemplary weak acids were loaded into pH gradient liposomes. The compounds were loaded using as a driving force the pH gradient generated by a transmembrane difference in acetate concentrations, as described in Example 3. The model compounds selected for loading, 5(6)-carboxyfluorescein and nalidixic acid, are both fluorescent weak acid compounds. Their fluorescent properties provided a useful means for determining the concentration of the compounds in liposomal media.

The fluorescence intensity of 5(6)-carboxyfluorescein and nalidixic acid is dependent on ionization state and compound concentration. The fluorescence of 5(6)-carboxyfluorescein increases with pH (Weinstein, et al., 1984), although the rise between pH 7 and pH 10 is only about 20%. The fluorescence of nalidixic acid at alkaline pH is 10 times lower than that measured at neutral pH. The fluorescence of both molecules is self-quenched at concentrations exceeding $10^{-3}$ M for 5(6)-carboxyfluorescein and $10^{-5}$ M for nalidixic acid.

Figure 4A:
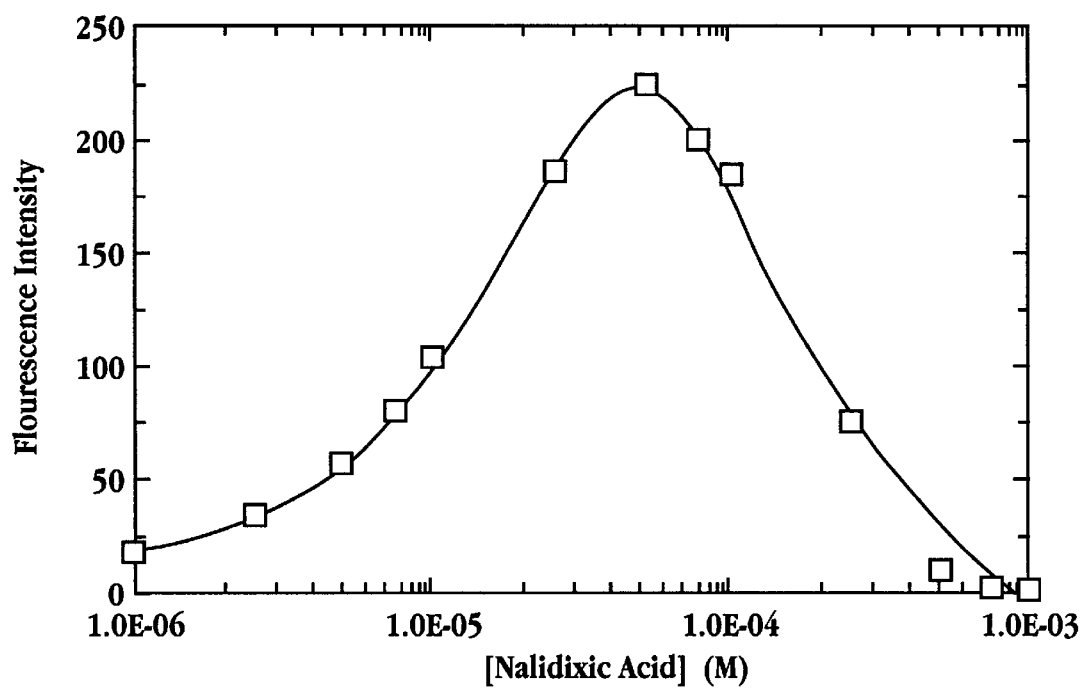
FIGS. 4A and 4B are plots showing the fluorescence intensity of solutions of nalidixic acid at concentrations ranging from $10^{-6}$ to $10^{-3}$ molar (FIG. 4A) and illustrates the self-quenching of nalidixic acid in 120 mM sodium sulfate solution at pH 7 (FIG. 4B)
Figure 4B:
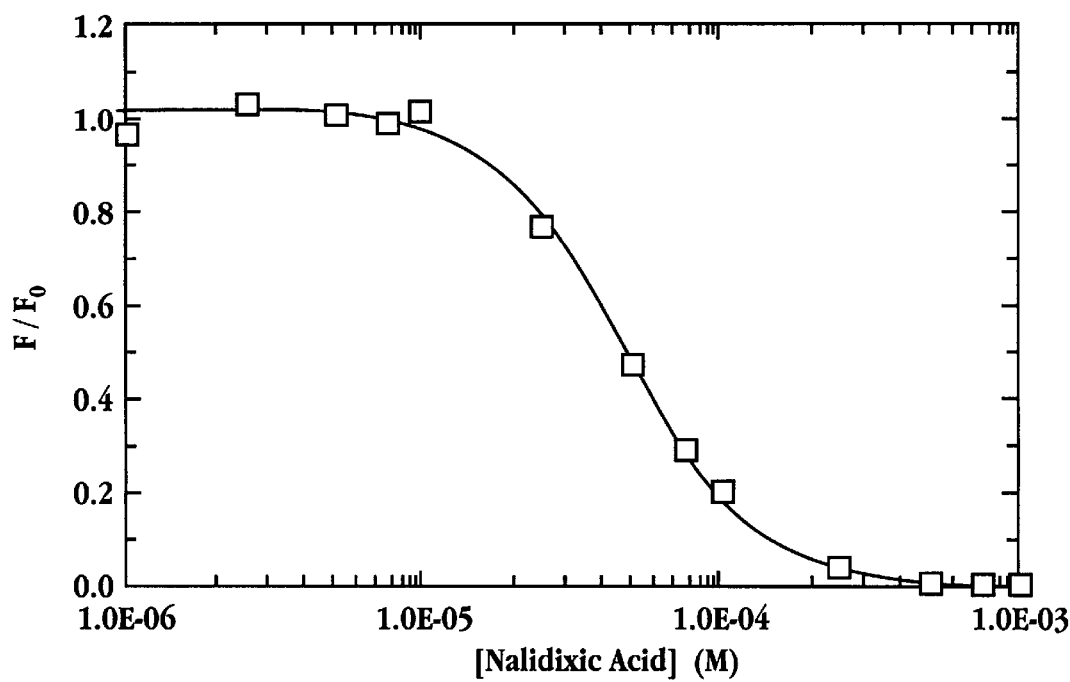

The fluorescence behavior of nalidixic acid as a function of concentration is illustrated in FIG. 4A. As can be seen from the figure, the fluorescence intensity of nalidixic acid is described by a bell shaped curve and reaches a maximum at $5 \times 10^{-5}$ M. At concentrations in the region below $10 \times^{-5}$ M, fluorescent intensity is linearly dependent on concentration. Self-quenching of nalidixic acid was determined from the ratio of measured fluorescence (F) to total fluorescence (Fo) and is plotted in FIG. 4B.

Figure 5A:
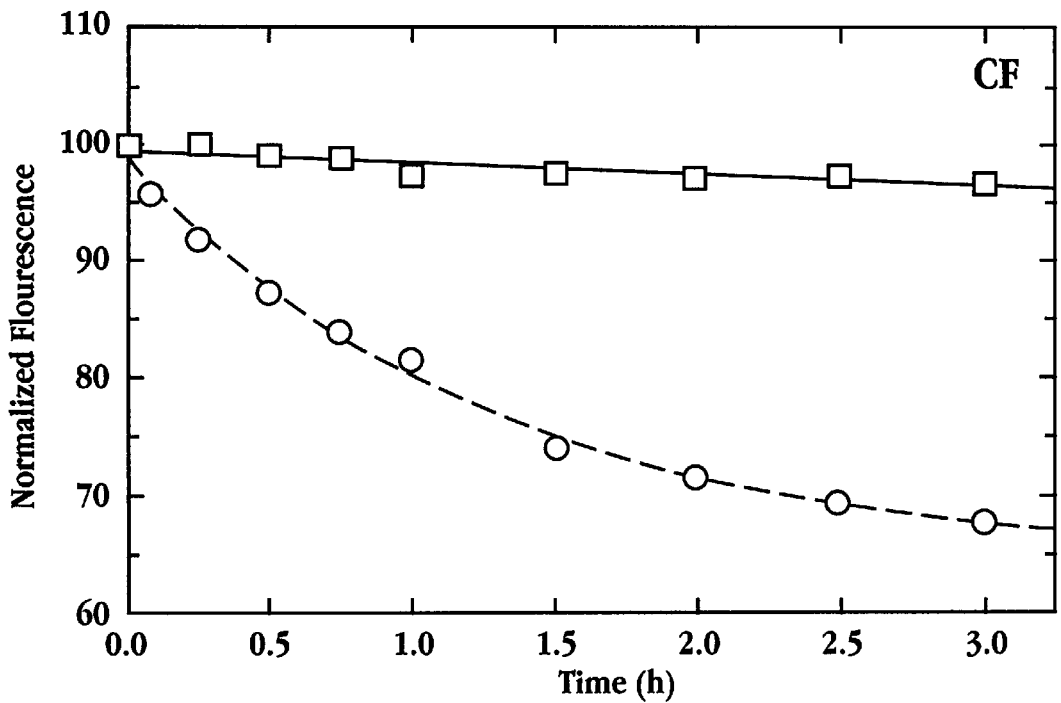
FIGS. 5A and 5B are plots showing the loading of two fluorescent weak acid drugs, 5(6)-carboxyfluorescein (FIG. 5A) and nalidixic acid (FIG. 5B) in the presence (broken line) and absence (solid line) of a transmembrane acetate gradient.
Figure 5B:
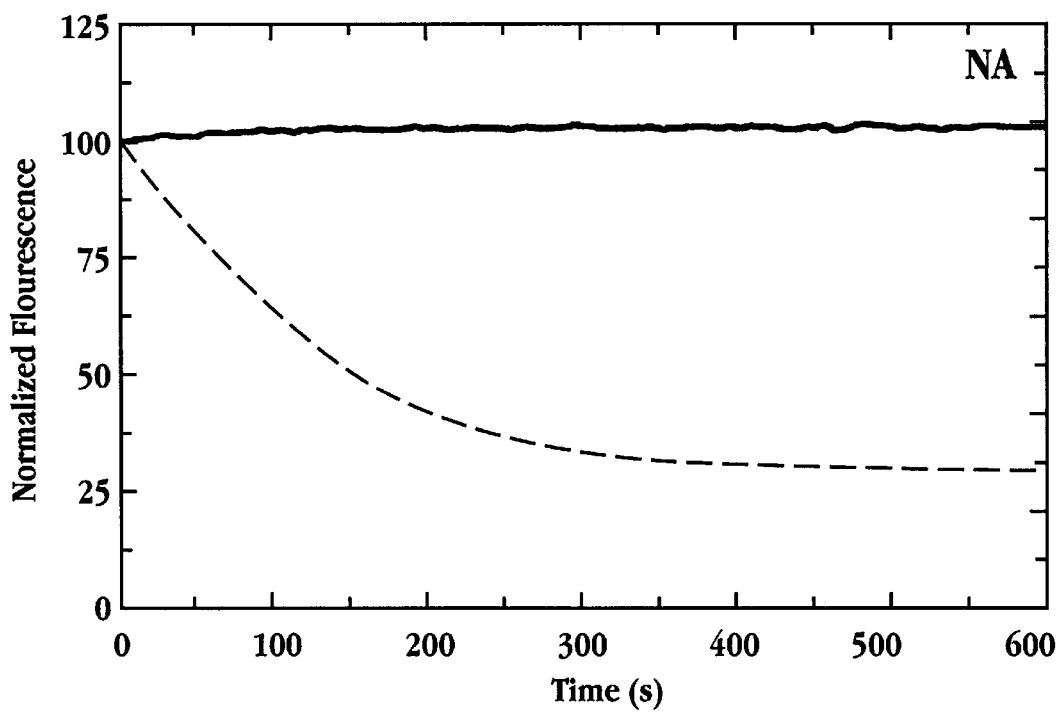

The loading behavior of the weak acid compounds in response to both acetate gradient and non-gradient liposomes is illustrated in FIGS. 5A, 5B and is described in Example 3B.

FIG. 5A illustrates the loading behavior of 5(6)-carboxyfluorescein. Briefly, incubation of a solution of 5(6)-carboxyfluorescein in aqueous calcium acetate (solid line/ boxes) with acetate-loaded liposomes resulted in no change in external concentration of the weak acid drug, suggesting that in the absence of a transmembrane ion gradient, the driving force for remote loading of the weak acid compound is removed. In contrast, when the acetate loaded liposomes are incubated in an aqueous sodium sulfate solution containing 5(6)-carboxyfluorescein (dotted line/circles), a rapid decrease in fluorescence was observed, indicating the uptake of the fluorescent weak acid compound into the liposome interior.

Similar results were observed for nalidixic acid (FIG. 5B) and indicate that in the absence of an acetate ion gradient, weak acid compounds are not effectively loaded into the liposome interior. The amount of weak acid compound that can be loaded increases with increasing transmembrane ion differential.

The studies above rely upon the fluorescence of 5(6)-carboxyfluorescein and nalidixic acid as an indicator of compound concentration. The fluorescence method was validated in separate experiments utilizing alternate analytical techniques as described in Example 3C.

The weak acid compounds, 5(6)-carboxyfluorescein and nalidixic acid, were each loaded into acetate gradient liposomes as detailed in Example 3C. 5(6)-carboxyfluorescein was incubated with acetate gradient liposomes for 17 hours (FIG. 6A, circles) or for 0 hours (control, squares) at 70° C. Nalidixic acid was similarly incubated with acetate gradient liposomes for 15 minutes at 25° C. (FIG. 6B, squares). The amount of each of the weak acid compounds entrapped in the liposome interior was directly determined by first separating trapped material from free material by gel exclusion chromatography, followed by detergent-promoted release of entrapped compound with Triton X100. The fluorescence intensity of each fraction was measured following detergent treatment.

Figure 6A:
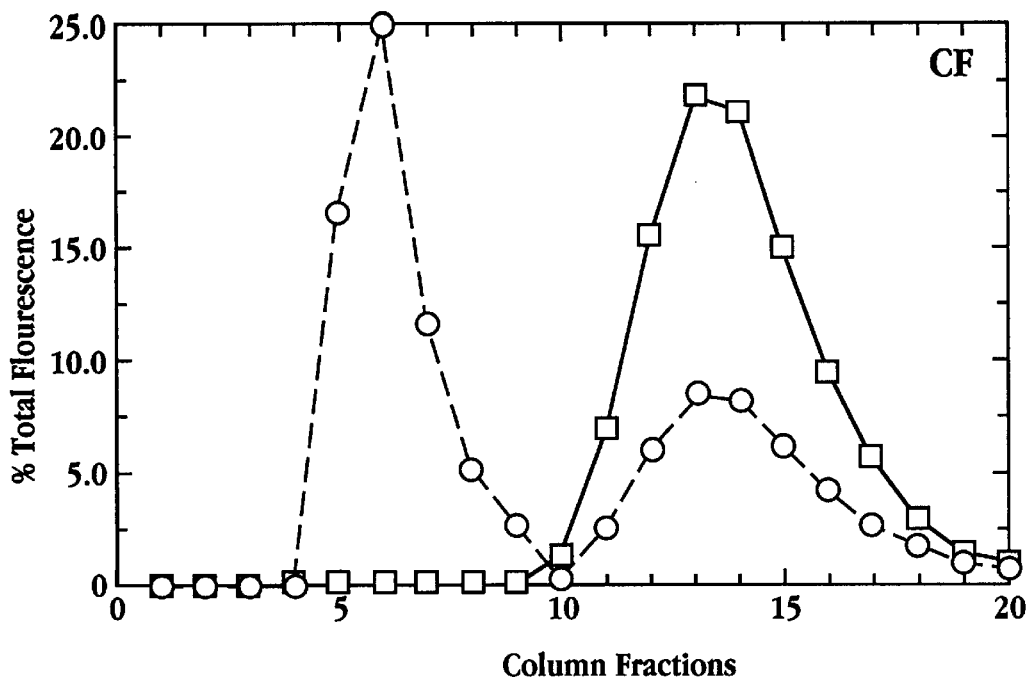
FIG. 6A is a gel exclusion chromatography profile of higher inside/lower outside acetate gradient liposomes incubated with 5(6)-carboxyfluorescein for either 17 hours (broken line) or 0 hours (solid line-control) at 70° C.
Figure 6B:
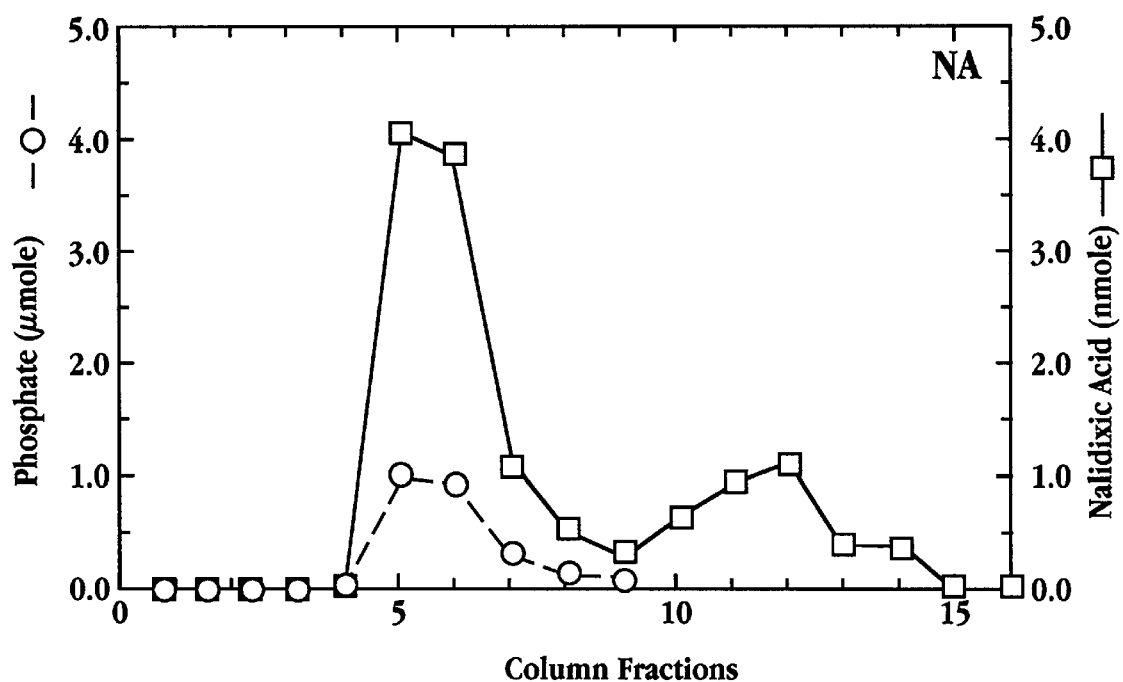
FIG. 6B is a gel exclusion chromatography profile of calcium acetate loaded vesicles incubated in 0.1 mM nalidixic acid for 15 minutes at 25° C.

The resulting gel exclusion profiles are shown in FIGS. 6A and 6B. As seen in FIG. 6A, about sixty percent of the total fluorescence eluted with 5(6)-carboxyfluorescein loaded liposomes, as evidenced by the ratio of fluorescence of the earlier eluting fractions 4–10 (indicating liposome-associated material) to the total (later eluting fractions 10–20 indicate untrapped compound).

A similar analysis of nalidixic acid revealed that seventy two percent of the total fluorescence was liposome-associated (FIG. 6B, squares). To further quantitate the amount of weak acid compound loaded into acetate gradient liposomes, the molar ratio of nalidixic acid to phospholipid was determined as described in Example 3C. As shown in FIG. 6B, the molar ratio of nalidixic acid to phospholipid (dotted line/circles) was determined to be about $4 \times 10^{-3}$. This corresponds to an internal concentration of nalidixic acid of about 1 mM, about ten times larger than the initial external concentration of weak acid compound.

In cases such as those described above in which drug loading is not effective to substantially deplete the external medium of free drug, the liposome suspension may be treated, following drug loading, to remove non-encapsulated drug. Free drug can be removed, for example, by molecular sieve chromatography, dialysis, or centrifugation.

However, with proper selection of liposome concentration, external concentration of added compound, and the pH gradient, essentially all of the weak acid compound may be loaded into the liposomes. For example, with a pH gradient of 2–3 units (or the potential of such a gradient employing an acetate ion gradient), the final internal:external concentration of drug will be about 1000:1. Knowing the calculated internal liposome volume, and the maximum concentration of loaded drug, one can then select an amount of drug in the external medium which leads to substantially complete loading into the liposomes.

Selective release of entrapped compound from the internal liposome compartment can be promoted by treating the liposomes as follows. As described in Examples 3D and 3F, release of entrapped nalidixic acid from the liposome interior was promoted by treating the liposomes with either Triton X-100 or a calcium ionophore, respectively.

As described in detail in Example 3D, a solution of nalidixic acid was added to acetate loaded vesicles (FIG. 7, t=100 s) and the resulting decrease in fluorescence was monitored as a function of time. As in the examples described above, a decrease in fluorescence can be attributed to the uptake of compound into the inner compartment of the liposomes.

Figure 7:
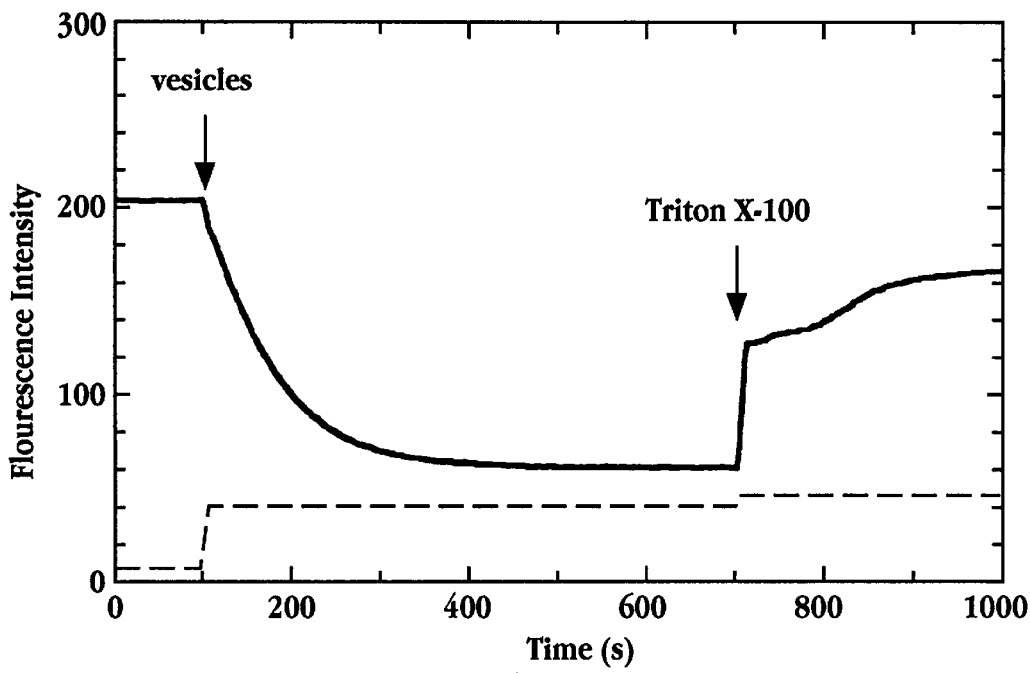
FIG. 7 is a plot showing release of entrapped nalidixic acid from liposomes upon permeabilization by addition of Triton X-100.

Upon addition of the detergent (t=700 s), a rapid increase in fluorescence was observed (FIG. 7, solid line), indicating the destruction of the integrity of the lipid bilayers and the release of nalidixic acid. The scattering caused by the vesicles was estimated under similar conditions but in the absence of nalidixic acid. The detergent did not have an effect on the light scattered by the liposomes (FIG. 7, broken line). This suggests that, in this instance, the permeabilization process involves the formation of holes in the membrane rather than the total disruption of the bilayer by formation of lipid-detergent micelles.

Another approach for releasing entrapped compound is to equilibrate the concentrations of acetate counterion (in this case, calcium) across the transmembrane barrier. As described in Example 3F, calcium acetate loaded liposomes were added at t=100 seconds to solutions of nalidixic acid maintained at 25° C. (FIG. 8, solid line) and 60° C. (broken line), respectively. The decrease in fluorescence was monitored over time, indicated loading of compound into the acetate gradient liposomes.

Figure 8:
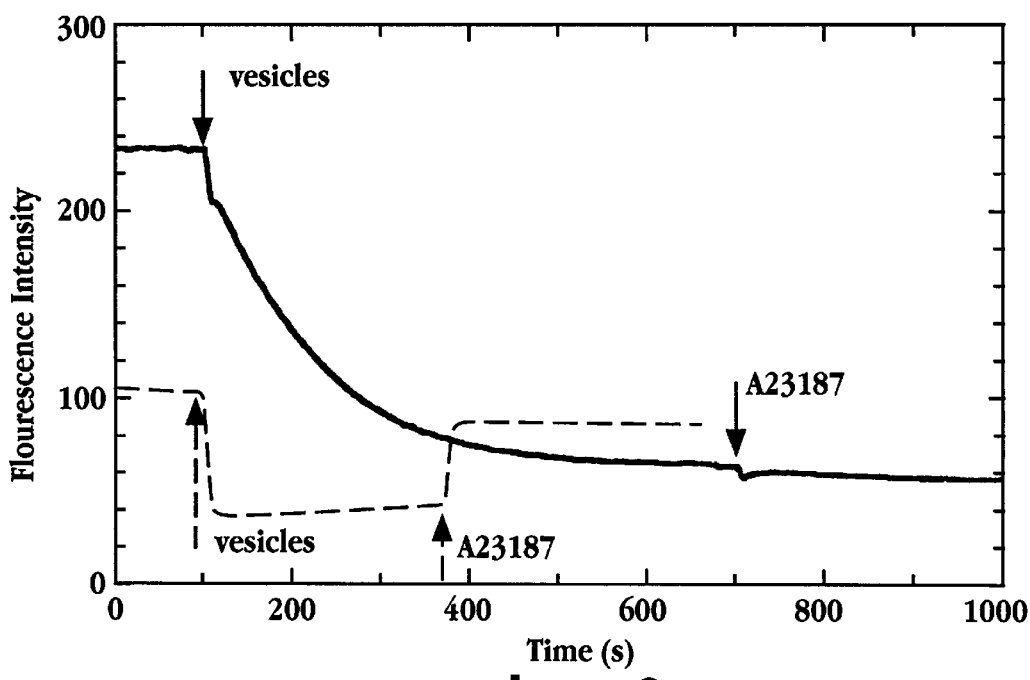
FIG. 8 is a plot showing release of entrapped nalidixic acid from liposomes maintained at 25° C. (solid line) and at 60° C. (broken line) by addition of the calcium ionophore, A23187.

The experiment was carried out at two different temperatures to investigate how changes in lipid phase (i.e., gel versus liquid-crystalline) affects the penetration of molecules into the bilayer. When the suspension was incubated at 25° C. (i.e., a temperature below the lipid phase transition temperature), addition of the ionophore at t=700 seconds had no effect on the fluorescence, as shown in FIG. 8 (solid line).

However, upon increasing the incubation temperature from 25° C. to 60° C., a significant effect on both the loading and the behavior of the ionophore was observed. Increasing the temperature above the lipid phase transition temperature during addition of the calcium ionophore resulted in a loading rate enhanced by one order of magnitude ($t_{1/2}$=84 s at 25° C. versus 7 s at 60° C.).

At 60° C., the calcium ionophore induced a rapid increase in fluorescence, explained by the release of the weak acid into the external medium. Equilibration of the calcium ion concentrations across the liposomal membrane resulted in the collapse of the driving force for loading and the subsequent release of entrapped compound.

D. Weak Acid Compounds for Liposome Loading

Compounds suitable for use with the present liposome loading method are weak acid drugs containing at least one carboxyl group. Although any weak acid compound may be used in the present invention, preferred classes of compounds belonging to this group include NSAID's, converting enzyme inhibitors, anti-microbial agents, and prostaglandins.

Non-steroidal anti-inflammatory compounds (NSAID's) are typically weak organic acids containing carboxyl moieties. Representative NSAID's for use in the invention include the salicylates, such as aspirin, propionic acid compounds, such as ibuprofen, indole derivatives such as indomethacin, fenamate compounds, such as meclofenamic acid and pyrrolealkanoic acid compounds such as tolmetin.

Adverse effects associated with some NSAID's include gastric intolerance, which may be minimized when such compounds are administered in liposome-encapsulated form. Such anti-inflammatory compounds are suitable for delivery by the liposome composition of the present invention, particularly by IV administration. The compound is useful, preferably, for treating inflammation and particularly for inflamed dermal tissue.

Another class of compounds belonging to those containing a derivatizable carboxyl group and for use in the present invention is the 6-fluoroquinolones, which have anti-microbial activity. Preferred drugs are those having a carboxyl function at the 3-position of the quinolone ring system and possessing antibacterial activity.

One preferred use for fluoroquinolone compounds is in the treatment of Mycobacterium infection, particularly *M. tuberculosis, M. kansasil, M. xenopi, M. fortuitum,* and *M. avium-M. intracellular* complex. Antibacterial quinolone agents are believed to penetrate into bacterial cells and inhibit DNA gyrase, an essential bacterial enzyme that maintains superhelical twists in DNA (Klopman, et al., 1993). One antibacterial agent for use in treating Mycobacterium infection, particularly M. avium-M. intracellulare, is ciprofloxacin.

Also included in this class of antimicrobials are the cephalosporins. Cephalosporins for use in the present invention are derivatives of 7-aminocephalosporanic acid possessing various substituents at the 3 and 7-positions and containing a carboxyl group at the 2 ring position. The cephalosporins typically have weights ranging from 400–450 and include cephalothin, cephalaxin, cefazolin, cephradine, cephapirin, cefamandole, and cefoxitin.

Depending upon the generation of drug, cephalosporins are known to be highly active against both gram-positive and gram-negative organisms. Many cephalosporins are active against E. coli, Klebsiella, and some strains of Proteus and Enterobacter.

The cephalosporins are typically administered intravenously since relatively few of the compounds are sufficiently well absorbed after oral intake to give systemic levels suitable for treatment. Cephalosporin drugs are particularly suited for liposomal administration for the treatment of infection, since liposomal delivery may reduce associated toxicity effects including anaphylaxis, urticaria and fever.

Another class of compounds suitable for use in the present invention are the prostaglandins. The basic structure common to all prostaglandins is "prostanoic acid", which consists of a cyclopentane ring with 2 aliphatic side chains, one of which terminates in a carboxyl group. There are 9 groups of prostaglandins, designated by the letters A–I.

The primary clinical applications of prostaglandin agents relate to their effects on smooth muscle. Due to their ability to contract uterine smooth muscle, prostaglandins are useful in gynecological applications, such as in inducing abortion or term labor. Prostaglandins may also be used for treating peripheral vascular disease or to block gastric acid secretion.

Another class of compounds suitable for use in the present invention are the converting enzyme inhibitors. Converting enzyme inhibitors are drugs that block the conversion of angiotensin I to angiotensin II and also inhibit the degradation of bradykinin, making these compounds useful as anti-hypertensive agents. Two such carboxyl-containing compounds suitable for use in the present invention are the L-proline derivatives captopril and enalapril.

The liposomes and compound used in practicing the method constitute a reagent combination for use in producing a suspension of liposomes with an encapsulated weak-acid compound, in accordance with another aspect of the invention. The combination includes liposomes of the type described in Section II, the weak-acid compound which, when added to a suspension of the liposomes, accumulates within the liposomes, and retaining means in the liposomes for retaining the compound that accumulates in the liposomes.

In the most general embodiment, the retaining means includes the weak-acid transmembrane gradient which is due to an excess of weak acid species in the liposomes after drug loading, and which provides a reservoir for sustaining the pH gradient, as discussed above.

Where the loaded compound is one which does not readily permeate the liposome membranes below the lipid phase transition temperature of the liposomes, the retaining means may additionally include the low-permeability barrier provided by the lipid bilayer.

Finally, where the loaded compound is one which has a low solubility in the presence of a selected cation, the cation itself provides retaining means by holding loading compound in a precipitated form that prevents efflux from the liposomes. In particular, it will be appreciated that the precipitating mechanism allows higher amounts of compound to be loaded stably into liposomes than is possible by a pH gradient alone, since the Henderson-Hasselbach relationship applies only to the solute form of the compound. For example, if the loaded compound precipitated above 5 mM compound concentration in the liposomes, a gradient effective to load to just above this relatively low concentration would be effective to load the liposomes to a high total compound concentration, e.g., 100–200 mM.

E. Compounds-Delivery Composition

Also included in the invention is the compound-loaded liposome composition formed by the above method, for use in delivering the loaded weak-acid compound. The composition includes, in an aqueous-suspension form, weak-acid gradient liposomes of the types described in Section II, the weak-acid compound encapsulated in the liposomes, by the loading method described in Section III, and retaining means in the liposomes for retaining the compound encapsulated in the liposomes, also as described in Section III.

The liposome composition may be used for a variety of drug-delivery applications, such as for delivering a drug or imaging agent intravenously for treating or imaging of a tumor, treating of infection, or depot delivery of the drug from the bloodstream. Where the liposomes are intended to circulate in the bloodstream over an extended period, e.g., for tumor targeting, they may be formed with a lipophilic polymer coating, such as a PEG coating, according to methods described above, and sized to a desired size range, e.g., 0.07–0.12 microns, also as described above.

It will be appreciated how the features of the invention contribute to its applications in drug-delivery or other uses of compound-loaded liposomes. The weak-acid gradient liposomes used for compound loading are effective to generate their own pH gradient, and self-sustain this gradient by the shifting equilibrium between protonated and non-protonated forms of the encapsulated weak acid.

Loading to high drug concentrations, and high efficiencies can be achieved by proper selection of external concentration of compound in relation to the weak-acid gradient and internal:external volume ratio in the liposome suspension. This loading can be carried out at a manufacturing site, or remotely at the site of use.

The liposomes, once loaded, are capable of retaining the compound at high concentration over an extended storage and/or drug-delivery period, by virtue of the self-sustaining gradient mechanism provided by the reservoir of weak acid in the liposomes. When coupled with other retaining means, including the use of high phase transition lipids and/or low compound solubility in the presence of the weak acid counterion, stable compound loading for periods of up to several months in suspension form may be achieved.

The following examples illustrate, but are in no way intended to limit the scope of the invention.

MATERIALS AND METHODS

Hydrogenated soybean phosphatidylcholine (HPC) was obtained from Lipoid KG (Ludwigshafen, Germany). 8-Hydroxypyrene-1,3,6-trisulfonic acid (pyranine), p-xylene-bis-pyridinium bromide (DPX) and 5(6)-carboxyfluorescein were purchased from Molecular Probes (Eugene, Oreg.). tert-Butanol was obtained from BDH Laboratory Supplies (Poole, England). Sephadex G-50 was obtained from Pharmacia (Uppsala, Sweden). HPLC-grade solvents were obtained from Labscan (Dublin, Ireland). Other standard chemical reagents and solvents were purchased from Sigma Chemical Co. (St. Louis, Mo.).

EXAMPLE 1

Preparation of Liposomes Containing Entrapped Acetate

A. Preparation of Lipid Vesicles

Hydrogenated soybean phosphatidylcholine and cholesterol (60:40 molar ratio) were prepared in a solution containing 0.5 mM pyranine and either i) 150 mM sodium acetate or ii) 120 mM calcium acetate, maintained at pH 6.0 and lyophilized overnight.

Untrapped pyranine was removed by gel-exclusion chromatography carried out using a Sephadex G-50 minicolumn preequilibrated with a solution of the corresponding acetate salt used to prepare the liposomes (i.e., 150 mM sodium acetate or 120 mM calcium acetate).

The resulting lipid mixture was hydrated at 70° C. (a temperature above the lipid "gel" state, i.e., to the liquid-crystalline or fluid phase transition temperature) to form multilamellar vesicles (MLVs). The volume of the hydration medium was adjusted to obtain a 10% (w/v) lipid concentration. The lipid suspension was frozen in liquid $N_2$, followed by thawing in a water bath maintained at 70° C. The freeze-thaw cycle was repeated five times.

B. Liposome Sizing

The vesicles were downsized by extrusion through two stacked 0.1 micron pore diameter polycarbonate filters (Poretics, Livermore, Calif.), using a "LIPOSOFAST" device built by Avestin (Ottawa, Canada) (MacDonald, et al., 1991). The vesicles were repeatedly extruded (15 extrusion cycles) at 70° C., with the extrusion apparatus maintained in an oven set at 70° C. Resulting vesicle size distributions were determined by quasielastic light scattering with a Coulter sub-micron particle analyzer (model N4 SD, Coulter Electronics, Luton, England). The phospholipid concentration was determined using a modified Bartlett procedure (Barenholz, et al., 1993).

Selected physical constants (dissociation constant ($pK_a$), permeability coefficient (P), and n-octanol/water partition coefficient ($K_p$) for acetic acid and pyranine are summarized in Table 1 below.

TABLE I

| Compound | pKa | P (cm/s) | Kp |
|---|---|---|---|
| acetic acid | 4.75[a] | $(6.6 \pm 1.3) \times 10^{-4}$[b] | 0.49[c] |
| pyranine | 7.22[d] | $<10^{-11}$[e] | $<3 \times 10^{-5}$ at pH 9 |

[a]Handbook of Chemistry and Physics, 73rd edition; CRC Press, Boca Raton, 1992.
[b]in egg phosphatidylcholine planar bilayer, at 22° C.; Walter and Gutknecht, 1984.
[c]at 25° C.; Wolosin and Ginsburg, 1975.
[d]Kano and Fendler, 1978.
[e]in 60/40 (mol/mol) HPC/cholesterol-extruded vesicles, at 25° C.

C. Determination of Internal pH

The internal pH of the liposomes was determined using a two-wavelength isosbestic-point method (Barreto, et al., 1992; Bolotin, et al., 1994) with a Perkin-Elmer LS 50B luminescence spectrometer. The fluorescence emission intensity at 507 nanometers was measured at excitation wavelengths of 460 and 415 nm. The lipid concentration in the cuvette was 0.03% (w/v). para-Xylene-bis-pyridinium bromide (DPX) was added to the lipid suspension at 2 mM final concentration to quench the fluorescence of residual untrapped pyranine.

A calibration curve was generated with pyranine (1 micromolar) dissolved in 120 mM calcium acetate at pH's ranging from 5.2 to 10.5 and is shown in FIG. 2A. The curve was used in subsequent experiments utilizing pyranine as a pH probe to determine internal liposome pH.

EXAMPLE 2

Formation of Liposomes Having a Transmembrane Acetate Gradient

Liposomes were prepared as described in Example 1 above. The liposomes were prepared in solutions of either i) 150 mM sodium acetate, pH 6.0 or ii) 120 mM calcium acetate, pH 6.0, corresponding to the respective internal concentrations of acetate salt. The acetate concentration in the external medium was then adjusted by one of the two following methods. In the first approach, the liposomes were diluted in a suspension containing 120 mM $Na_2SO_4$, 2 mM DPX, and the corresponding acetate salt used to prepare the liposomes. Alternatively, the external medium was adjusted by gel-exclusion chromatography on Sephadex G-50 mini-columns preequilibrated with 120 mM $Na_2SO_4$.

The concentration of sodium sulfate was adjusted to 120 mM to maintain the same osmolality on both sides of the lipid bilayers. Solution osmolalities were measured using a Wescor 5500 vapor pressure osmometer (Wescor Inc., Logan, Utah).

Internal pH values were calculated from the entrapped pyranine fluorescence as described in Example 1C. A plot showing the changes in internal pH as a function of acetate ion gradient is shown in FIG. 2B.

EXAMPLE 3

Gradient Loading of (6)-Carboxyfluorescein and Nalidixic Acid into Liposomes

A. Physical Properties of 5(6)-Carboxyfluorescein and Nalidixic Acid

Two weak acid compounds, 5(6)-carboxyfluorescein and nalidixic acid, were selected for remote loading into pH gradient liposomes. Properties of the weak acids are given in Table II below.

TABLE II

| Molecules | pKa | P (cm/s) | Kp |
|---|---|---|---|
| 5(6)-carboxy-fluorescein | 6.3[a] | $8.1 \times 10^{-11}$ at pH 7[b]<br>$7.2 \times 10^{-13}$ at pH 8.2 | $2.8 \times 10^{-3}$ at pH 6.9[c]<br>$6.0 \times 10^{-5}$ at pH 8.0 |
| nalidixic acid | 6.13[d] | $1.4 \times 10^{-8}$ at 25° C.[e]<br>$1.7 \times 10^{-7}$ at 60° C. | $3.34 \pm 0.08$ at pH 7[f] |

[a]Weinstein, et al., 1984.
[b]in egg phosphatidylcholine, at 37° C.; Weinstein, et al., 1984.
[c]Grimes, et al., 1942.
[d]Takacs-Novák, et al., 1990.
[e]in 60/40 (mol/mol) HPC/cholesterol-extruded vesicles.
[f]Tsuji, et al., 1988.

B. Liposome Loading

5(6)-carboxyfluorescein (1 micromolar) was dissolved in either i) 120 mM calcium acetate at pH 7.0 or in ii) 120 mM sodium sulfate, 1.2 mM calcium acetate at pH 7.0 and incubated in the presence of lipid vesicles loaded with calcium acetate (0.033% w/v final lipid concentration).

Nalidixic acid (0.1 mM) was dissolved in either i) 120 mM sodium sulfate at pH 7.0 or in ii) 150 mM sodium acetate at pH 7.0 (dashed line) and similarly incubated in the presence of lipid vesicles loaded with calcium acetate (0.033% w/v final lipid concentration). The fluorescence intensity of the resulting suspensions were monitored as a function of time and normalized to the values measured at time 0 (FIGS. 5A and 5B).

C. Quantitation of the Amount of 5(6)-Carboxyfluorescein and Nalidixic Acid Loaded into Liposomes 5(6)-Carboxyfluorescein loaded liposomes were prepared by incubating a solution of 5(6)-carboxyfluorescein (1.4 mM initial external concentration in 120 mM sodium sulfate) with calcium acetate loaded vesicles for either zero or 17 hours at 70° C.

Nalidixic acid loaded liposomes were similarly prepared by incubating calcium acetate loaded vesicles in a solution of nalidixic acid (0.1 mM initial external concentration in 120 mM sodium sulfate) for 15 minutes at 25° C.

Trapped weak acid compounds were separated from the free material by gel-exclusion chromatography. The fluorescence intensity (excitation: 470 nm; emission: 520 nm) of each eluent fraction was measured after addition of Triton X-100 (3 mM final concentration). The results are shown in FIGS. 6A (squares: 0 hour incubation; circles: 17 hour incubation) and 6B (squares: nalidixic acid; circles: phospholipid phosphate) for 5(6)-carboxyfluorescein and nalidixic acid, respectively.

D. Quantification of Nalidixic Acid Concentration

1. HPLC. The amount of nalidixic acid present in the vesicle suspensions was quantified by HPLC (Vallée, et al., 1986). The samples were extracted with 9/1 (v/v) methylene chloride/2-propanol and eluted on an Alltech C-18 reversed-phase column (Alltech Applied Science Labs, State College, Pa.) (150 mm length; 4.6 mm ID). A mobile phase containing: 65/35 (v/v) methanol/55 mM $K_2PO_4$; 18 mM $Na_2HPO_4$; and 5.5 mM hexadecyltrimethyl-ammonium bromide, pH 7.4 was used. The flow rate was 1.0 ml/min. Detection was carried out by UV absorption at 328 nm. Under these conditions, the retention time of nalidixic acid was typically 5.1 min.

2. Fluorescence and Self-Quenching of Nalidixic Acid. Solutions of varying concentrations of nalidixic acid in 120 mM sodium sulfate, pH 7.0, were prepared and the fluorescence intensity of each was determined. The results are plotted in FIGS. 4A and 4B.

E. Detergent-Promoted Release of Entrapped Nalidixic Acid

Triton X-100 was added to a suspension of nalidixic acid loaded liposomes. At t=100 s, calcium acetate loaded vesicles (0.033% w/v final lipid concentration) were added to a 0.1 mM solution of nalidixic acid. At t=700 s, Triton X-100 (5 mM final concentration) was added to the liposomal suspension. The fluorescence intensity was monitored over the course of the experiment (excitation: 328 nm; emission: 364 nm) at 25° C. as a function of time. The results are shown in FIG. 7.

F. Calcium-Promoted Release of Entrapped Nalidixic Acid

At t=100 s, calcium acetate loaded vesicles (0.033% w/v final lipid concentration) were added to a solution containing $10^{-4}$ M nalidixic acid. A calcium ionophore, A23187, (10 micromolar) was added at either t=700 s (25° C.; FIG. 8—solid line) or at 350 s (60° C.; FIG. 8—broken line), and the fluorescence was monitored over the course of the experiment. The results are shown in FIG. 8.

Compounds suitable for use with the present liposome loading method are weak acid drugs containing at least one carboxyl group. Although any weak acid compound may be used in the present invention, preferred classes of compounds belonging to this group include NSAID's, converting enzyme inhibitors, antimicrobial agents, and prostaglandins.

Although the invention has been described with respect to particular embodiments and methods, it will be appreciated that various changes and modifications can be made without departing from the invention.

It is claimed:

1. A method of forming liposomes having a higher inside/lower outside pH gradient, comprising:

preparing a suspension of liposomes in an aqueous solution of a weak acid salt comprising (i) an anion, which, in protonated form, is uncharged and is capable of freely permeating the transmembrane barrier of liposomes, and (ii) a counterion that is substantially lipid membrane impermeable, adjusting the concentration of weak acid salt present in the external medium to produce a higher inside/lower outside concentration gradient of the weak acid salt, and allowing the weak acid to distribute itself between inner and outer liposome compartments, with the weak acid acting as an inside-to-outside proton shuttle, thereby generating a higher inside/lower outside pH gradient.

2. The method of claim 1, wherein the weak acid is a carboxylic acid selected from the group consisting of formic acid, acetic acid, propanoic acid, butanoic acid, and pentanoic acid.

3. The method of claim 2, wherein the carboxylic acid is acetic acid.

4. The method of claim 1, wherein said adjusting comprises replacing the salt of the weak acid in the external medium with the salt of a strong acid.

5. The method of claim 4, whereby said replacing is effective to raise the osmolality of the external medium to a value substantially equal to that of the internal medium.

6. A method of loading a weak-acid compound into liposomes, comprising:

adding the compound to a suspension of liposomes having a higher inside/lower outside gradient of a weak acid salt comprising (a) an anion, which, in protonated form is uncharged and is capable of readily permeating the transmembrane barrier of the liposomes, and (b) a counterion that is substantially lipid membrane impermeable, wherein the weak acid acts as an inside-to-outside proton shuttle to generate a higher inside/lower outside pH gradient and an accumulation of the compound within the liposomes, and by said adding, achieving uptake of the compound within the liposomes.

7. The method of claim 6, wherein the weak acid is a carboxylic acid selected from the group consisting of formic, acetic, propanoic, butanoic, and pentanoic acid.

8. The method of claim 7, wherein the carboxylic acid is acetic acid.

9. The method of claim 6, wherein the weak-acid compound has a low water solubility in the presence of a given cation, and the counterion of the weak acid salt comprises said cation, whereby the weak acid compound is accumulated within the liposomes in precipitated form.

10. The method of claim 9, wherein the compound loaded into the liposomes is selected from the group consisting of nonsteroidal antiinflammatory drugs, 6-fluoroquinolones, cephalosporins, prostaglandins, and angiotensin converting enzyme inhibitors.

11. The method of claim 6, wherein (i) the compound in protonated form is readily able to permeate the liposome transmembrane barrier only at a temperature above the phase transition temperature of the liposomes, (ii) the compound and suspension are maintained at a temperature above the phase transition temperature during compound accumulation into the liposomes, and (iii) said method further comprises cooling the compound and suspension below such transition temperature after compound loading into the liposomes.

12. The method of claim 11, wherein said compound is selected from the group consisting of non-steroidal anti-inflammatory drugs, 6-fluoroquinolones, cephalosporins, prostaglandins, and angiotensin converting enzyme inhibitors.

* * * * *